United States Patent
Ikeda et al.

(10) Patent No.: US 8,377,995 B2
(45) Date of Patent: Feb. 19, 2013

(54) ORALLY DISINTEGRATING TABLET

(75) Inventors: Yuki Ikeda, Ibaraki (JP); Yasushi Ochiai, Ibaraki (JP)

(73) Assignee: Dainippon Sumitomo Pharma Co., Ltd., Osaka-shi (JP)

( * ) Notice: Subject to any disclaimer, the term of this patent is extended or adjusted under 35 U.S.C. 154(b) by 0 days.

(21) Appl. No.: 12/743,871

(22) PCT Filed: Nov. 21, 2008

(86) PCT No.: PCT/JP2008/071254
§ 371 (c)(1),
(2), (4) Date: May 20, 2010

(87) PCT Pub. No.: WO2009/066773
PCT Pub. Date: May 28, 2009

(65) Prior Publication Data
US 2010/0286286 A1 Nov. 11, 2010

(30) Foreign Application Priority Data
Nov. 21, 2007 (JP) ................................. 2007-302284

(51) Int. Cl.
*A01N 25/00* (2006.01)
*A61K 47/00* (2006.01)
(52) U.S. Cl. ....................................................... 514/770
(58) Field of Classification Search .................. None
See application file for complete search history.

(56) References Cited

U.S. PATENT DOCUMENTS

| | | | |
|---|---|---|---|
| 6,596,311 B1 * | 7/2003 | Dobetti | 424/464 |
| 2008/0274178 A1 | 11/2008 | Imamoto et al. | |

FOREIGN PATENT DOCUMENTS

| | | |
|---|---|---|
| CN | 1303284 A | 7/2011 |
| EP | 1927347 A1 | 6/2008 |
| JP | 05-032627 A | 2/1993 |
| JP | 2001-069961 A | 3/2001 |
| JP | 2001-069961 A | 5/2001 |
| JP | 2002-505269 A | 2/2002 |
| JP | 2007-238451 A | 9/2007 |
| WO | WO 99/44580 A1 | 9/1999 |
| WO | WO 00/02560 A1 | 1/2000 |
| WO | WO 03/075918 A1 | 9/2003 |
| WO | WO 2005/123040 A1 | 12/2005 |
| WO | WO 2007/018190 A1 | 2/2007 |
| WO | WO 2007/018192 A1 | 2/2007 |

OTHER PUBLICATIONS

Pamphlets by Kyowa Chemical Industry Co., Ltd., "Anhydrous Calcium Hydrogen Phosphate GS," vols. 1-12 (Aug. 2006-May 2007).
Fu et al., *Critical Reviews in Therapeutic Drug Carrier Systems*, 21(6): 433-475 (2004).
Chinese Intellectual Property Office (CIPO), First Office Action in Chinese Patent Application No. 200880117311.9 (Jun. 22, 2011).

* cited by examiner

*Primary Examiner* — Patricia A Duffy
*Assistant Examiner* — Garen Gotfredson
(74) *Attorney, Agent, or Firm* — Leydig, Voit & Mayer, Ltd.

(57) ABSTRACT

The invention provides an orally disintegrating tablet that has both adequate tablet hardness and rapid disintegrability in the oral cavity, and that undergoes minor hardness reduction and maintains good oral disintegrability even when preserved under moist conditions. In particular, the invention relates to an orally disintegrating tablet containing (a) crystalline cellulose, (b) a calcium hydrogen phosphate compound, (c) a natural starch and (d) a lubricant, wherein the blending ratio to 100 wt % of the disintegrating tablet is (a) 9 to 60 wt %, (b) 16 to 60 wt %, (c) 3 to 40 wt % and (d) 0.01 to 1.8 wt %.

15 Claims, No Drawings

ORALLY DISINTEGRATING TABLET

TECHNICAL FIELD

The present invention relates to an orally disintegrating tablet that disintegrates rapidly in the oral cavity even when taken with a small amount of water or without water, particularly to an orally disintegrating tablet that undergoes minor hardness reduction and maintains good disintegrability even under moist conditions.

BACKGROUND ART

Orally disintegrating tablets are tablets that disintegrate rapidly in the oral cavity even when taken without water, and are a preparation easily ingestible even by elderly people with decreased capability of swallowing.

In recent years, there have been active efforts at hospitals and dispensing pharmacies for improving drug compliance for patients taking a plurality of medicines by setting the plurality of medicines in a single package for each intake time zone to prevent the patient from failing to take a medicine, or from erroneously taking an incorrect medicine. For this reason, before the patient takes a medicine, the drug is sometimes exposed to moist conditions as is taken out from the package or PTP sheet. Because orally disintegrating tablets, in particular, generally have low tablet hardness, it is feared that the tablet can break before intake, or the disintegration time is delayed, if the tablet hardness decreases due to exposure to moist conditions. For this reason, there is a demand for the creation of an orally disintegrating tablet that undergoes minor hardness reduction and maintains disintegrability even when stored under moist conditions in medical practice settings.

An orally disintegrating tablet often contains a sugar alcohol used as an excipient to secure disintegrability. However, if the tablet ingredients contained in the orally disintegrating tablet include a substance that reacts with sugar alcohols to produce an impurity, it is desirable that the tablet ingredients be substantially free from sugar alcohols.

In this situation, regarding orally disintegrating tablets that do not contain sugar alcohols as essential ingredients, and that contain crystalline cellulose and anhydrous calcium hydrogen phosphate as excipients, Patent Documents 1 to 5 and Non-patent Document 1 shown below are known.

The orally disintegrating tablet described in Patent Document 1 consists essentially of an active ingredient, crystalline cellulose and an inorganic excipient such as anhydrous calcium hydrogen phosphate, and is characterized by the absence of a disintegrant. Furthermore, it is stated that the orally disintegrating tablet of Patent Document 1 is less likely to undergo hardness reduction and disintegration time delay under moist conditions, compared with orally disintegrating tablets containing a disintegrant such as crospovidone or croscarmellose sodium (Example 5 and Comparative Examples 5 to 9). There is another statement, "Because disintegrants have tablet quality deteriorating properties, such as causing tablet hardness reductions and tablet surface roughness as a result of moisture absorption, and worsening the mouth touch due to a feeling of dryness as a result of saliva absorption, the present invention, which does not contain a disintegrant, is advantageous."

Described in Patent Document 2 is an orally disintegrating tablet containing an active ingredient, crystalline cellulose, an inorganic excipient such as anhydrous calcium hydrogen phosphate, carmellose and a lubricant at 0.8 wt % or less. In the orally disintegrating tablet, it is essential to use carmellose as a disintegrant, and the use of a disintegrant like natural starch as a disintegrant is not described at all.

Patent Document 3 relates to a rapidly disintegrating tablet containing a water-insoluble inorganic excipient, a disintegrant, and a substantially water-soluble excipient, and discloses an orally disintegrating tablet containing anhydrous calcium hydrogen phosphate, corn starch, crystalline cellulose and magnesium stearate. However, the blending ratio of anhydrous calcium hydrogen phosphate and the blending ratio of magnesium stearate in the orally disintegrating tablet differ from the blending ratio of a calcium hydrogen phosphate compound and the blending ratio of a lubricant in the orally disintegrating tablet of the present invention described below. Incidentally, the absolute hardness of the orally disintegrating tablet described in Patent Document 3 (tensile strength as determined by squashing in diameter direction) is 0.7 N/mm$^2$ or less.

Disclosed in Patent Document 4 is a tablet containing crystalline cellulose, calcium hydrogen phosphate, corn starch, and magnesium stearate; the blending ratio of calcium hydrogen phosphate and the blending ratio of magnesium stearate differ from the blending ratio of a calcium hydrogen phosphate compound and the blending ratio of a lubricant in the orally disintegrating tablet of the present invention described below.

Patent Document 5 relates to a bitterness-suppressed preparation; disclosed in Example 34 thereof is a preparation containing granules obtained by agitation granulating an efficacy ingredient, corn starch and hydroxypropylmethylcellulose, crystalline cellulose, calcium hydrogen phosphate and magnesium stearate.

Described in Non-patent Document 1 is an orally disintegrating tablet containing crystalline cellulose, anhydrous calcium hydrogen phosphate, and, as a disintegrant, croscarmellose sodium or carmellose. However, the use of a natural starch as used in the present invention described below as a disintegrant is not described at all. Nor is there any description of the suppression of hardness reduction and disintegration time delay under moist conditions, which are the problems to be solved by the present invention described below.

Described in Patent Document 6 are a spray-dried composition of calcium hydrogen phosphate and erythritol, a composition for bitterness masking containing an umami ingredient, and an orally disintegrating tablet containing these compositions. Disclosed in an Example in the specification is an orally disintegrating tablet containing crystalline cellulose, calcium hydrogen phosphate, corn starch, and a lubricant at 1 wt % or less; however, the present invention described below, which does not contain erythritol as an essential ingredient, is distinct from the orally disintegrating tablet, for which it is essential to spray-dry a suspension of calcium hydrogen phosphate and erythritol. Furthermore, the invention described in Patent Document 6 intends to mask the bitterness of bitter ingredients, and the suppression of hardness reduction and disintegration time delay under moist conditions, which are the problems to be solved by the present invention described below, is not described at all.

Patent Document 1: WO2005/123040
Patent Document 2: WO2007/018192
Patent Document 3: JP-A-2002-505269
Patent Document 4: JP-A-HEI-5-32627
Patent Document 5: WO2007/018190
Patent Document 6: JP-A-2001-69961
Non-patent Document 1: Pamphlet by Kyowa Chemical Industry Co. Ltd. (Report on anhydrous calcium hydrogen phosphate GS)

DISCLOSURE OF THE INVENTION

Problems to Be Solved by the Invention

Provided is an orally disintegrating tablet that has both adequate hardness and rapid disintegrability in the oral cavity, and that undergoes minor hardness reduction and maintains good oral disintegrability under moist conditions.

Means for Solving the Problems

The present inventors conducted extensive investigations to solve the above-described problems, and found that an orally disintegrating tablet comprising, in addition to crystalline cellulose and a calcium hydrogen phosphate compound, a natural starch as a disintegrant and a lubricant at 1.8 wt % or less, possesses adequate hardness and undergoes minor hardness reduction and maintains good oral disintegrability under moist conditions, compared with conventionally known orally disintegrating tablets.

Accordingly, the present invention relates to the following.
Item 1: An orally disintegrating tablet comprising (a) crystalline cellulose, (b) a calcium hydrogen phosphate compound, (c) a natural starch and (d) a lubricant, wherein the blending ratio to 100 wt % of the disintegrating tablet is (a) 9 to 60 wt %, (b) 16 to 60 wt %, (c) 3 to 40 wt % and (d) 0.01 to 1.8 wt %.
Item 2: The orally disintegrating tablet described in Item 1, wherein the blending ratio of the crystalline cellulose (a) is 9 to 53 wt %, and the blending ratio of the natural starch (c) is 3 to 30 wt %.
Item 3: The orally disintegrating tablet described in Item 1 or 2, wherein the tablet further comprises an efficacy ingredient (e) at a blending ratio of 0.01 to 60 wt %.
Item 4: The orally disintegrating tablet described in one item of Items 1 to 3, wherein the tablet further comprises one or more additives selected from the group consisting of fillers, binders, sweetening agents, taste correctives/odor correctives, fragrances, fluidizing agents, antistatic agents, coloring agents and coating agents.
Item 5: The orally disintegrating tablet described in Item 3 or 4, wherein the tablet consists essentially of crystalline cellulose (a), a calcium hydrogen phosphate compound (b), a natural starch (c), a lubricant (d) and an efficacy ingredient (e).
Item 6: The orally disintegrating tablet described in Item 3, wherein the tablet is obtained by adding a lubricant (d) to a composition obtained by blending crystalline cellulose (a), a calcium hydrogen phosphate compound (b) and a natural starch (c), each of which is in a powder or granular form, and an efficacy ingredient (e), and compression-molding the composition.
Item 7: The orally disintegrating tablet described in one item of Items 1 to 5, wherein the tablet is produced by compression molding by direct tableting.
Item 8: The orally disintegrating tablet described in one item of Items 1 to 7, wherein the blending ratio of the crystalline cellulose (a) is 20 to 53 wt %.
Item 9: The orally disintegrating tablet described in one item of Items 1 to 8, wherein the blending ratio of the calcium hydrogen phosphate compound (b) is 30 to 60 wt %.
Item 10: The orally disintegrating tablet described in one item of Items 1 to 9, wherein the blending ratio of the natural starch (c) is 9 to 30 wt %.
Item 11: The orally disintegrating tablet described in one item of Items 1 to 10, wherein the blending ratio of the lubricant (d) is 0.01 to 1.0 wt %.
Item 12: The orally disintegrating tablet described in Item 4, wherein the blending ratio of the additive is 0.01 to 40 wt %.
Item 13: The orally disintegrating tablet described in one item of Items 1 to 12, wherein the natural starch (c) is at least one kind selected from the group consisting of corn starch, wheat starch, rice starch and potato starch.
Item 14: The orally disintegrating tablet described in Item 13, wherein the natural starch (c) is corn starch.
Item 15: The orally disintegrating tablet described in one item of Items 1 to 14, wherein the lubricant (d) is at least one kind selected from the group consisting of stearic acid, calcium stearate, sodium stearyl fumarate, talc, light anhydrous silicic acid and magnesium stearate.
Item 16: The orally disintegrating tablet described in Item 15, wherein the lubricant (d) is magnesium stearate.

EFFECT OF THE INVENTION

Obtained according to the present invention is an orally disintegrating tablet that possesses both adequate hardness and rapid disintegrability in the oral cavity, and that undergoes minor hardness reduction and maintains good oral disintegrability even under moist conditions.

For this reason, it is possible to provide an orally disintegrating tablet that exhibits sufficient tablet hardness and good disintegrability in the oral cavity even if the tablet is exposed to moist conditions in medical practice settings or commercial distribution processes.

BEST MODE FOR CARRYING OUT THE INVENTION

Hereinafter, the present invention is described in further detail.

(a) Crystalline Cellulose

The crystalline cellulose used in the present invention is not particularly limited, as far as it permits oral administration. If the average particle diameter of the crystalline cellulose is large, roughness to the tongue is felt after disintegration in the oral cavity; therefore, from the viewpoint of the feeling of taking the medicine, the average particle diameter of the crystalline cellulose for a raw material is preferably 150 μm or less, more preferably 130 μm or less, still more preferably 120 μm or less. If the bulk density of the crystalline cellulose for a raw material is small, oral disintegration time after humidification tends to be extended, so the bulk density of the crystalline cellulose is preferably 0.1 to 0.5 g/cm$^3$, more preferably 0.25 to 0.5 g/cm$^3$. The bulk density is measured by untapped apparent density using the Scott Volumeter.

The blending ratio of the crystalline cellulose used in the present invention is, from the viewpoint of hardness and disintegration time, 9 to 60 wt %, preferably 9 to 59 wt %, more preferably 9 to 53 wt %, still more preferably 20 to 53 wt %, relative to the total tablet weight.

As mentioned herein, a blending ratio indicates a ratio of each ingredient to total tablet weight taken as 100 wt %.

As examples of the crystalline cellulose used in the present invention, CEOLUS (registered trademark, PH-101, PH-102, PH-301, PH-302, PH-F20J, KG-800, KG-1000, ST-02: manufactured by Asahi Kasei Chemicals Corporation), AVICEL (registered trademark, PH-101, PH-102, PH-301, PH-302, FD-101, FD-301, FD-F20: manufactured by FMC BioPolymer), CELPHERE SCP (Asahi Kasei Chemicals Corporation), PHARMACEL (PHARMACEL 101, 102: GOKYO TRADING CO., LTD.) can be mentioned.

These crystalline celluloses may be used alone, and may also be used in combination of two kinds or more.

(b) Calcium Hydrogen Phosphate Compounds

The calcium hydrogen phosphate compounds used in the present invention include calcium hydrogen phosphate (dibasic calcium phosphate), anhydrous calcium hydrogen phosphate (anhydrous dibasic calcium phosphate), and calcium dihydrogen phosphate (monobasic calcium phosphate). These calcium hydrogen phosphate compounds are not particularly limited, as far as they permit oral administration. The blending ratio of the calcium hydrogen phosphate compounds used in the present invention is, from the viewpoint of hardness and disintegration time, 16 to 60 wt %, preferably 30 to 60 wt %, relative to the total tablet weight.

As an example of the calcium hydrogen phosphate used in the present invention, calcium hydrogen phosphate (standard, FF: manufactured by Kyowa Chemical Industry Co., Ltd.) can be mentioned. As examples of the anhydrous calcium hydrogen phosphate used in the present invention, anhydrous calcium hydrogen phosphate (GS, GSH, heavy, standard, light: manufactured by Kyowa Chemical Industry Co., Ltd.) and FUJICARIN (registered trademark, manufactured by FUJI CHEMICAL INDUSTRY CO., LTD.) can be mentioned.

If the drug substance is unstable to water, it is preferable to use anhydrous calcium hydrogen phosphate. When a mixed powder of raw materials is directly tableted to produce tablets, calcium hydrogen phosphate and anhydrous calcium hydrogen phosphate for direct tableting are effective. As an example of calcium hydrogen phosphate for direct tableting, calcium hydrogen phosphate (FF: manufactured by Kyowa Chemical Industry Co., Ltd.) can be mentioned. As an example of anhydrous calcium hydrogen phosphate for direct tableting, anhydrous calcium hydrogen phosphate (GS, GSH: manufactured by Kyowa Chemical Industry Co., Ltd.) can be mentioned.

As examples of the calcium dihydrogen phosphate used in the present invention, monobasic calcium phosphate (manufactured by Tohoku Kagaku Kogyo) and calcium dihydrogen phosphate (manufactured by KOKUSAN CHEMICAL CO., LTD., manufactured by JUNSEI CHEMICAL CO., LTD., manufactured by Taihei Chemical Industrial Co., Ltd., manufactured by HAYASHI PURE CHEMICAL IND., LTD., manufactured by YONEYAMA CHEMICAL INDUSTRY CO., LTD.) can be mentioned.

As the above-described calcium hydrogen phosphate compounds, one or two or more selected from the group consisting of calcium hydrogen phosphate, anhydrous calcium hydrogen phosphate and calcium dihydrogen phosphate can be used.

(c) Natural Starches

As the natural starches used in the present invention, natural starches such as corn starch, potato starch, rice starch, wheat starch, sweet potato starch, mung bean starch, and tapioca starch can be mentioned. These natural starches may be used alone, and may also be used in combination of two kinds or more. Of them, corn starch, potato starch, wheat starch, and rice starch are preferable because of the high suppressive effect on delay of disintegration after humidification. Cornstarch is more preferable from the viewpoint of hardness and disintegrability after humidification.

The blending ratio of the natural starches is, from the viewpoint of hardness and disintegration time, 3 to 40 wt %, preferably 3 to 30 wt %, still more preferably 9 to 30 wt %, relative to the total tablet weight.

As examples of the natural starches, corn starch (Corn Starch (XX16)W: manufactured by NIHON SHOKUHIN KAKO CO., LTD., corn starch: manufactured by San-Ei Gen F.F.I., Inc., manufactured by JUNSEI CHEMICAL CO., LTD., manufactured by NIPPON STARCH CHEMICAL CO., LTD., manufactured by Matsutani Chemical Industry Co., Ltd.), wheat starch (Matsutani Kiku: manufactured by Matsutani Chemical Industry Co., Ltd.), rice starch (nonglutinous rice starch (Micropearl), rice cake powder starch (Motyl B): manufactured by Shimada Kagaku Kogyo), potato starch (Matsutani Himawari: manufactured by Matsutani Chemical Industry Co., Ltd., manufactured by JUNSEI CHEMICAL CO., LTD., manufactured by NIPPON STARCH CHEMICAL CO., LTD.), sweet potato starch (manufactured by Matsutani Chemical Industry Co., Ltd.), mung bean starch (manufactured by Matsutani Chemical Industry Co., Ltd.), and tapioca starch (Matsutani Sakura: manufactured by Matsutani Chemical Industry Co., Ltd.) can be mentioned.

(d) Lubricants

As lubricants used in the present invention, magnesium stearate, calcium stearate, stearic acid, sodium stearyl fumarate, talc, light anhydrous silicic acid, sucrose fatty acid esters, and polyethylene glycol can be mentioned, with preference given to magnesium stearate, calcium stearate, stearic acid, sodium stearyl fumarate, talc, and light anhydrous silicic acid, more preferably magnesium stearate. These lubricants may be used alone, and may be used in combination of two kinds or more.

In the present invention, the lubricant may be formulated using whichever method of external lubrication and internal lubrication.

The blending ratio of lubricant is 0.01 to 1.8 wt %, preferably 0.01 to 1.0 wt %, more preferably 0.01 to 0.8 wt %, particularly preferably 0.1 to 0.5 wt %, relative to the total tablet weight. A tendency was observed wherein as the lubricant content decreases, the tablet hardness is more likely to be restored, and the hardness retention rate increases when the tablet was returned to a low-humidity environment after humidification. When the lubricant content is high, disintegration time after humidification tends to be delayed; particularly, if the blending ratio of the lubricant exceeds 2 wt %, disintegration time after humidification is 30 seconds or more. Meanwhile, if the lubricant content is lower than 0.01%, tableting failures are likely to occur. The above-described lubricant can also be used in a blending ratio of 0.25 to 0.95 wt %.

(e) Efficacy Ingredients

The efficacy ingredient used in the orally disintegrating tablet of the present invention may be any efficacy ingredient. The efficacy ingredient used in the present invention is not particularly limited, as far as it permits oral administration. For example, nutritious tonics; antipyretic analgesic anti-inflammatory drugs; antipsychotic drugs; hypnotic sedatives; antispasmodic drugs; central nervous system drugs; brain metabolism ameliorators; brain circulation ameliorators; anti-epileptic drugs; sympathomimetic drugs; stomachic digestants; anti-ulcer agents; gastrointestinal tract movement ameliorators; antacids; antitussive expectorants; intestinal movement suppressants; antiemetics; respiratory stimulants; bronchodilators; anti-allergic drugs; antihistaminic agents; cardiotonics; anti-arrhythmic agents; diuretics; ACE inhibitors; Ca antagonists; AII antagonists; vasoconstrictors; coronary vasodilators; vasodilators; peripheral vasodilators; antihyperlipidemic agents; choleretic drugs; cephem antibiotics; oral antibacterial drugs; chemotherapeutic agents; sulfonylurea drugs; α glucosidase inhibitors; insulin resistance ameliorators; rapid-acting insulin secretagogues; DPPIV inhibitors; diabetic complication remedies; anti-osteoporosis agents; antirheumatic agents; skeletal muscle relaxants; alkaloid narcotics; sulfa drugs; goat remedies; blood coagulation inhibitors; anti-malignancy agents, and the like can be mentioned.

Specifically, as the efficacy ingredient in the present invention, nutritious tonics such as vitamins, minerals, amino acids, crude drugs, and lactobacilli; antipyretic analgesic anti-inflammatory drugs such as aspirin, acetaminophen, ethenzamide, ibuprofen, caffeine, and indomethacin; antipsychotic drugs such as blonanserin, lurasidone hydrochloride, tandospirone citrate, perospirone hydrochloride, reserpine, diazepam, fludiazepam, haloperidol, aripiprazole, and nortriptyline hydrochloride; hypnotic sedatives such as nitrazepam, diazepam, triazolam, brotizolam, zolpidem, and nimetazepam; antispasmodic drugs such as scopolamine hydrobromide; central nervous system drugs such as zonisamide, droxidopa, citicoline, biperiden hydrochloride, and donepezil hydrochloride; brain metabolism ameliorators such as meclofenoxate hydrochloride; brain circulation ameliorators such as vinpocetine; anti-epileptic drugs such as zonisamide, phenytoin, clonazepam, primidone, sodium valproate, carbamazepine, diazepam, ethotoin, and acetylpheneturide; sympathomimetic drugs such as isoproterenol hydrochloride; stomachic digestants such as diastase, scopolia extract, and pancreatin; anti-ulcer agents such as cimetidine, lansoprazole, famotidine, sulpiride, and gefarnate; gastrointestinal tract movement ameliorators such as mosapride citrate; antacids such as magnesium aluminometasilicate; antitussive expectorants such as chloperastine hydrochloride, ephedrine hydrochloride, and pentoxyverine citrate; intestinal movement suppressants such as loperamide hydrochloride; antiemetics such as difenidol hydrochloride; respiratory stimulants such as levallorphan tartrate; bronchodilators such as theophylline; anti-allergy drugs such as ebastine; antihistaminic agents such as diphenhydramine hydrochloride; cardiotonics such as caffeine and digoxin; anti-arrhythmic agents such as procainamide hydrochloride and arotinolol hydrochloride; diuretics such as isosorbide; ACE inhibitors such as delapril hydrochloride, captopril, and alacepril; Ca antagonists such as nifedipine, diltiazem hydrochloride, manidipine hydrochloride, and amlodipine besilate; AII antagonists such as candesartan, olmesartan, and valsartan; vasoconstrictors such as phenylephrine hydrochloride; coronary vasodilators such as carbochromen hydrochloride; vasodilators such as limaprost alfadex; peripheral vasodilators such as cinnarizine; antihyperlipidemic agents such as simvastatin and pravastatin sodium; choleretic drugs such as dehydrocholic acid; cephem antibiotics such as cefalexin and cefaclor; oral antibacterial drugs such as gatifloxacin and suparfloxacin; chemotherapeutic drugs such as sulfamethizole and pipemidic acid trihydrate; sulfonylurea drugs such as gliclazide, glibenclamide, and glimepiride; α-glucosidase inhibitors such as acarbose, voglibose, and miglitol; such as insulin resistance ameliorators such as pioglitazone hydrochloride and rosiglitazone; biguanides such as metformin, buformin, and fenformin; rapid-acting insulin secretagogues such as nateglinide and mitiglinide calcium hydrate; DPPIV inhibitors such as sitagliptin; diabetic complication remedies such as ranirestat and epalrestat; anti-osteoporosis agents such as etidronate disodium; antirheumatic agents such as methotrexate; skeletal muscle relaxants such as methocarbamol; anti-vertiginous drugs such as meclizine hydrochloride; alkaloid narcotics such as morphine hydrochloride and opium; sulfa drugs such as sulfisomidine; goat remedies such as allopurinol; blood coagulation inhibitors such as dicoumarol; anti-malignancy agents such as 5-fluorouracil and mitomycin, and the like can be mentioned.

The efficacy ingredient in the present invention may be selected from among indomethacin, blonanserin, lurasidone hydrochloride, tandospirone citrate, perospirone hydrochloride, fludiazepam, haloperidol, nortriptyline hydrochloride, nimetazepam, zonisamide, droxidopa, biperiden hydrochloride, phenyloin, clonazepam, primidone, sodium valproate, ethotoin, acetylpheneturide, pancreatin, cimetidine, sulpiride, gefarnate, mosapride citrate, ephedrine hydrochloride, pentoxyverine citrate, arotinolol hydrochloride, alacepril, amlodipine besilate, gatifloxacin, suparfloxacin, pipemidic acid trihydrate, gliclazide, miglitol, lanilestat, etidronate disodium, allopurinol and the like.

The efficacy ingredients mentioned above may be in the form of salts or free entities other than those mentioned above, as far as they are pharmaceutically acceptable. The efficacy ingredients may also be in the form of solvates such as alcohol solvates, or hydrates and the like. The blending ratio of the efficacy ingredient in the present invention is understood to include salts included in the above-described efficacy ingredients, solvents of solvates, and/or water in hydrates. Furthermore, the efficacy ingredients mentioned above may be used singly, or may be used in combination of two kinds or more. The efficacy ingredients may also be used after being subjected to a treatment for masking the unpleasant tastes such as bitterness of the efficacy ingredient. As examples of masking, coating of an efficacy ingredient can be mentioned.

As mentioned herein, coating refers to coating all or part of the surface of an efficacy ingredient with a coating ingredient. As apparatuses for this coating, ordinary fluidized-bed granulating machine (including rotor fluidized-bed granulating machine, Wurster fluidized-bed granulating machine and the like) can be mentioned; to suppress particle coarsening in a step, preference is given to improved Wurster fluidized-bed granulating machines equipped with an apparatus for forced circulation from side (for example, SPC, manufactured by POWREX CORPORATION, and the like), hybrid fluidized-bed granulating machines equipped with a grinding mechanism (screen impeller type, blade stator type, cross-screws, lump breakers and the like) (for example, super fine particle coating and granulating processor SFP-01, manufactured by POWREX CORPORATION, and the like), and rotary fluidized-bed granulating machines (for example, OMNITECS, manufactured by NARA MACHINERY CO. LTD., and the like). As apparatuses for spray drying, ordinary spray dryers (manufactured by OKAWARA CORPORATION, manufactured by OHKAWARA KAKOKI CO. LTD., manufactured by Yamato, manufactured by Niro, and the like) can be used.

When using a substance that undergoes interaction with sugar alcohols in an orally disintegrating tablet, it is feared that an impurity may be produced in the tablet; however, the orally disintegrating tablet of the present invention is free from the fear of such incompatibility with other ingredients because sugar alcohols are unessential, so the substance can be used effectively as an efficacy ingredient or additive. For example, a drug having a carboxyl group is feared to undergo a dehydration reaction with a sugar alcohol to produce an impurity; however, in the case of the orally disintegrating tablet of the present invention, there is no fear that such a dehydration reaction may occur because sugar alcohols are unessential. Additionally, the orally disintegrating tablet of the present invention can have adequate hardness even when tableted at lower tableting pressures compared with conventional orally disintegrating tablets based on sugar alcohol, so the orally disintegrating tablet of the present invention is also effective when a coated drug that is likely to have its coat destructed by the pressure during tableting is used as an efficacy ingredient.

The blending ratio of an efficacy ingredient is, from the viewpoint of hardness and disintegration time, normally 0.01 to 60 wt %, preferably 0.01 to 50 wt %, more preferably 0.01 to 25 wt %, particularly preferably 0.01 to 10 wt %, relative to the total tablet weight.

Additives

The tablet of the present invention may further comprise various additives in common use for tablet manufacture as required. Although the additives can be used, as far as the disintegrability and moldability of the orally disintegrating tablet of the present invention are not affected, the blending ratio of the additive is normally 0.01 to 40 wt %, preferably 0.01 to 20 wt %, more preferably 0.01 to 10 wt %.

As examples of the additives, fillers, binders, sweetening agents, taste correctives/odor correctives, fragrances, fluidizing agents, antistatic agents, coloring agents and coating agents can be mentioned. In addition to natural starches, disintegrants that do not influence the effect of the present invention may be added as additives. The above-described additives may be used singly, or may be used in mixture of two kinds or more in an optionally chosen ratio.

As examples of the above-described filler, xylitol, sorbitol, trehalose, glucose, white soft sugar, lactose hydrates, calcium sulfate, and calcium carbonate can be mentioned.

As examples of the above-described binder, gum arabic, gum arabic powder, partially gelatinized starch, gelatin, agar, dextrin, pullulan, povidone, polyvinyl alcohol, ethylcellulose, carboxymethylethylcellulose, carmellose, carmellose sodium, hydroxyethylcellulose, hydroxyethylmethylcellulose, hydroxypropylcellulose, and hydroxypropylmethylcellulose can be mentioned.

As examples of the above-described sweetening agents, aspartame, acesulfame potassium, fructose, reduced maltose syrup, dipotassium glycyrrhizinate, saccharin, saccharin sodium, sucralose, stevia, and thaumatin can be mentioned.

As examples of the above-described taste correctives/odor correctives, amino acids and salts thereof such as sodium aspartate, alanine, arginine, glycine, glutamine, arginine glutamate, glutamic acid hydrochloride, and sodium glutamate, organic acids such as adipic acid, ascorbic acid, citric acid, succinic acid, tartaric acid, and malic acid, licorice, triethyl citrate, taurine, and tannic acid can be mentioned.

As examples of the above-described fragrances, orange essence, orange oil, caramel, camphor, cinnamon oil, spearmint oil, strawberry essence, chocolate essence, cherry flavor, spruce oil, pine oil, pennyroyal oil, vanilla flavor, bitter essence, fruit flavor, peppermint essence, mix flavor, mint flavor, menthol, lemon powder, lemon oil, and rose oil can be mentioned.

As examples of the above-described fluidizing agents, hydrated silicon dioxide, light anhydrous silicic acid, heavy anhydrous silicic acid, and titanium dioxide can be mentioned.

As examples of the above-described antistatic agents, hydrated silicon dioxide, light anhydrous silicic acid, and talc can be mentioned.

As examples of the above-described coloring agents, food colors such as Food Color Red No. 3, Food Color Yellow No. 5, and Food Color Blue No. 1, yellow ferric oxide, red ferric oxide, brown iron oxide, black iron oxide, copper chlorophyll, copper chlorophyll sodium, riboflavin, and green powdered tea can be mentioned.

As examples of the above-described coating agents, ethyl acrylate-methyl methacrylate copolymer dispersion liquids, aminoalkyl methacrylate copolymer, gum arabic powder, ethylcellulose, Opadry, carnauba wax, carboxyvinyl polymer, carboxymethylethylcellulose, carmellose sodium, dry methacrylic acid copolymer, stearyl alcohol, cetanol, shellac, gelatin, hydroxypropylcellulose, hydroxypropylmethylcellulose acetate succinate, hydroxypropylmethylcellulose, pullulan, povidone, polyvinyl alcohol, hydroxyethylcellulose, hydroxyethylmethylcellulose, polyvinyl alcohol copolymer, dimethylaminoethyl methacrylate-methyl methacrylate copolymer, hydroxypropylmethylcellulose phthalate, fumaric acid-stearic acid-polyvinylacetal diethylaminoacetate-hydroxypropylmethylcellulose mixture, polyvinylacetal diethylaminoacetate, methacrylic acid copolymer, and 2-methyl-5-vinylpyridine methylacrylate-methacrylic acid copolymer can be mentioned.

Orally Disintegrating Tablets

In the present invention, an orally disintegrating tablet means a tablet that disintegrates rapidly in the oral cavity even when taken without water, usually a tablet that disintegrates only with the saliva in the oral cavity within 30 seconds (preferably within 28 seconds, more preferably within 25 seconds). It is recommended that the orally disintegrating tablet have a level of tablet hardness that does not produce cracking or defects when taken out from the PTP. Specifically, the orally disintegrating tablet of the present invention has an absolute hardness of 1.0 N/mm$^2$ or more, preferably 1.5 N/mm$^2$ or more, more preferably 2.0 N/mm$^2$ or more. Absolute hardness is a value calculated from hardness measured using a tablet hardness tester and tablet cross section area (=diameter×thickness) as follows.

$$\text{Absolute hardness [N/mm}^2\text{]=hardness [N]÷(tablet diameter [mm]×tablet thickness [mm])}$$

Furthermore, the orally disintegrating tablet of the present invention is an orally disintegrating tablet that undergoes a little hardness reduction even when stored under moist conditions. For example, even when the orally disintegrating tablet is stored at 40° C. and a relative humidity of 75% for 3 days, its absolute hardness is 1.0 N/mm$^2$ or more, preferably 1.5 N/mm$^2$ or more, more preferably 2.0 N/mm$^2$ or more.

Used herein as an index of the degree of maintenance of hardness before humidification (an index indicating the degree of hardness reduction suppression after humidification) was hardness retention rate as indicated by the equation shown below.

$$\text{Hardness retention rate (\%)=absolute hardness after humidification absolute hardness before humidification×100}$$

In the present invention, the hardness retention rate, for example, when the moist conditions is storage at 40° C. and a relative humidity of 75% for 3 days, is normally 50% or more, preferably 53% or more, more preferably 55% or more, most preferably 60% or more.

In the present invention, "an orally disintegrating tablet consisting essentially of (a) crystalline cellulose, (b) a calcium hydrogen phosphate compound, (c) a natural starch, (d) a lubricant and (e) an efficacy ingredient" means an orally disintegrating tablet that may contain in addition to (a) crystalline cellulose, (b) a calcium hydrogen phosphate compound, (c) a natural starch, (d) a lubricant and (e) an efficacy ingredient, the above-described additives, as far as the effect of the present invention is not affected. Specifically, the blending ratio of the additive is normally 0.01 to 40 wt %, preferably 0.01 to 20 wt %, more preferably 0.01 to 10 wt %. However, if the additive includes a disintegrant other than natural starches, the blending ratio of the disintegrant other than the natural starches is 0.01 to 5 wt %.

In the present invention, "crystalline cellulose (a), a calcium hydrogen phosphate compound (b) and a natural starch (c), each of which is in a powder or granular form" means crystalline cellulose (a), a calcium hydrogen phosphate compound (b) and a natural starch (c) wherein each of the ingredients of crystalline cellulose (a), a calcium hydrogen phosphate compound (b), and a natural starch (c) consists of a single ingredient in a powder or granular form without being granulated with other ingredients.

In medical practice settings such as dispensing pharmacies, ambient environmental changes are likely. Regarding humidity, in particular, drugs can be exposed to a moist environment due to an influence of weather in time zones where air-conditioning is not in operation.

In medical practice settings under these conditions, it is desirable to create an orally disintegrating tablet that maintains tablet physical properties even after taken out from the PTP package or drug package; to this end, however, it is desirable that not only "hardness after humidification" meet a specified criterion, but also the alteration due to moistening be small, that is, the "hardness retention rate" be high. The fact that the "hardness retention rate" is low means that the change in the tablet inside environment upon moistening is large, which in turn is likely to cause tablet cracks and defects.

Even if the orally disintegrating tablet is exposed to a moist environment at a time out of operating hours in medical practice settings, cracks and defects are unlikely to occur during all-in-one packaging work using a tablet packaging machine, provided that the hardness is restored as the humidity is controlled at low levels during operating hours, so this is substantially unproblematic.

In the present invention, for example, when the moist conditions are cyclic storage involving repeats of moistening and drying (at 25° C. and a relative humidity of 75% for 3 days, at 25° C. and a relative humidity of 11% for 1 day, at 25° C. and a relative humidity of 75% for 3 days, at 25° C. and a relative humidity of 11% for 1 day), the hardness retention rate is preferably 70% or more, more preferably 75% or more, most preferably 80% or more.

A feature of the present invention resides in the fact that not only before humidification, but also after humidification, a high tablet hardness and an adequate disintegration time are exhibited, and that the difference in tablet hardness between before humidification and after humidification is small, that is, the hardness retention rate is high. Specifically, the orally disintegrating tablet of the present invention meets the requirements that the absolute hardness before humidification and after humidification should be 1.0 N/mm$^2$ or more, the oral disintegration time before humidification and after humidification should be within 30 seconds, and the hardness retention rate should be 50% or more. More preferably, the orally disintegrating tablet of the present invention meets the requirements that the absolute hardness before humidification and after humidification should be 1.5 N/mm$^2$ or more, the oral disintegration time before humidification and after humidification should be within 30 seconds, and the hardness retention rate should be 55% or more. More preferably, the orally disintegrating tablet of the present invention meets the requirements that the absolute hardness before humidification and after humidification should be 2.0 N/mm$^2$ or more, the oral disintegration time before humidification and after humidification should be within 28 seconds, and the hardness retention rate should be 60% or more. Most preferably, the orally disintegrating tablet of the present invention meets the requirements that the absolute hardness before humidification and after humidification should be 2.0 N/mm$^2$ or more, the oral disintegration time before humidification and after humidification should be within 25 seconds, and the hardness retention rate should be 60% or more. As examples of the above-described moist conditions, storage at 40° C. and a relative humidity of 75% for 3 days can be mentioned.

The method of producing the orally disintegrating tablet of the present invention is not particularly limited, and may be an optionally chosen one. For example, the tablet can be obtained by blending crystalline cellulose, a calcium hydrogen phosphate compound, a natural starch, an optionally chosen efficacy ingredient, a lubricant, and, as required, additives, and thereafter directly compression-molding the mixture (that is, direct tableting). Specifically, a method can be mentioned wherein a lubricant (d) is added to a composition obtained by blending crystalline cellulose (a), a calcium hydrogen phosphate compound (b) and a natural starch (c), each of which is powder or granular form, and an efficacy ingredient (e), and compression-molding the composition. The efficacy ingredient (e) may be used after being coated by a method known per se for the purpose of bitterness masking, drug release control such as by sustained release preparation, drug stabilization, and productivity improvement (for example, fluidity improvement, blendability improvement, tableting failure prevention) and the like. In cases where the content uniformity of the efficacy ingredient is affected, such as by the aggregating property or large crystal size of each ingredient used, each tablet ingredient may be adjusted to a particle diameter that ensures content uniformity by means of a technique such as milling before mixing or after mixing. As required, the mixture may be granulated with a binder, and thereafter compression-molded.

Generally, tablets are often produced in away such that the tablet water content will be low in consideration of drug stability. In the present invention, a tendency is observed wherein the tablet hardness retention rate can be kept at high levels by having a high water content in the tablet just after tableting. Although the tablet water content after tableting is not particularly limited, the water activity value is preferably 0.3 to 0.9 aw, more preferably 0.6 to 0.8 aw. As mentioned here, the water activity value is expressed from the ratio of the water vapor pressure (P) of the tight container containing the composition and the pure water vapor pressure (P$_0$) at that temperature, as shown in the following equation.

$$\text{Water activity value} = P \div P_0$$

Water activity values can be measured using an apparatus, for example, a portable water activity meter (Pawkit, manufactured by Decagon Devices) and the like. To adjust the tablet water content just after tableting, the step of compression molding may be preceded by the step of moistening the composition.

The method of shaping the orally disintegrating tablet of the present invention is not particularly limited; compression molding methods with the use of a rotary tableting machine, single punch tableting machine or oil hydraulic press machine and the like is used. Compression molding pressure is not particularly limited, as far as it confers sufficient strength to the tablet.

The shape of the tablets used in the present invention is not particularly limited; the tablets may assume any of the forms of round-shaped tablets, round-shaped R-tablets, round-shaped beveled edge tablets, various irregular-shaped tablets and the like, and may be prepared as scored tablets.

The orally disintegrating tablet of the present invention permits direct tableting after raw materials are blended, and can be produced by a simple method such as granulation;

because the orally disintegrating tablet does not require a special step such as spray drying, the manufacturing operation is simple, and the orally disintegrating tablet is economical in terms of manufacturing cost.

EXAMPLES

The present invention is explained in more detail in the following by referring to Examples and Comparative Examples, which are not to be construed as limitative.

In the Examples, the anhydrous calcium hydrogen phosphate, corn starch, magnesium stearate and carmellose used were those mentioned below unless particularly specified.

Anhydrous calcium hydrogen phosphate (GS: manufactured by Kyowa Chemical Industry Co., Ltd.), magnesium stearate (light, plant: manufactured by Taihei Chemical Industrial Co., Ltd.), corn starch (corn starch (XX16)W: manufactured by NIHON SHOKUHIN KAKO CO., LTD.), carmellose (NS-300: manufactured by Gotoku Yakuhin).

Crystalline cellulose used had various average of bulk densities mentioned below. In the following Examples, the trade names are indicated. CEOLUS PH-101 (0.29 g/cm$^3$), CEOLUS PH-102 (0.30 g/cm$^3$), CEOLUS PH-301 (0.41 g/cm$^3$), CEOLUS PH-302 (0.43 g/cm$^3$), CEOLUS KG-802 (0.21 g/cm$^3$), CEOLUS PH-F20J (0.23 g/cm$^3$) (all manufactured by Asahi Kasei Chemicals Corporation, the numbers in parentheses show the average of bulk density).

As an oil hydraulic press to be used for punching tablets, a handy forming machine TB-20H (manufactured by NPa SYSTEM CO., LTD.) was used.

The tablet hardness and oral disintegration time of the tablets obtained in Examples and Comparative Examples were measured by the following test methods.

Tablet hardness: Using a tablet hardness tester (TH-203MP: manufactured by Toyama Sangyo Co., Ltd.), the force necessary for squashing a tablet in the diameter direction was measured. Using hardness value measured by the tablet hardness tester, the absolute hardness was calculated from the following formula.

absolute hardness [N/mm$^2$]=hardness [N]÷(tablet diameter [mm]×tablet thickness [mm])

Oral disintegration time: A tablet was placed in the mouth cavity, and time before complete disintegration of the tablet was measured. After the test, the content was spit out, and the mouth cavity was washed with clean water.

Comparative Example 1

Formulation without Disintegrant

Crystalline cellulose (CEOLUS PH-101), anhydrous calcium hydrogen phosphate and magnesium stearate were mixed at ratios shown in Table 1. The obtained mixture was applied to an oil hydraulic press to give tablets (tableting conditions: tableting pressure 6 kN, 120 mg/tablet, diameter 7 mm, round shape with beveled edge).

TABLE 1

Table 1 Formulation without disintegrant formulation ratio (wt %)

| component | Comp. Ex. 1-1 | Comp. Ex. 1-2 | Comp. Ex. 1-3 | Comp. Ex. 1-4 | Comp. Ex. 1-5 | Comp. Ex. 1-6 | Comp. Ex. 1-7 |
|---|---|---|---|---|---|---|---|
| crystalline cellulose | 79.4 | 69.4 | 59.5 | 49.6 | 39.7 | 29.8 | 19.8 |
| anhydrous calcium hydrogen phosphate | 19.8 | 29.8 | 39.7 | 49.6 | 59.5 | 69.4 | 79.4 |
| magnesium stearate | 0.8 | 0.8 | 0.8 | 0.8 | 0.8 | 0.8 | 0.8 |
| total | 100.0 | 100.0 | 100.0 | 100.0 | 100.0 | 100.0 | 100.0 |

Using the obtained tablets, the tablet hardness and oral disintegration time were measured before and after humidification under 40° C. relative humidity 75% conditions for 3 days. The obtained results are shown in Table 2. Before humidification, the tablets were good and showed hardness of 1.0 N/mm$^2$ or above and disintegration time of within 30 seconds, but the tablets after humidification showed oral disintegration time of more than 100 seconds and failed to maintain good disintegration property.

TABLE 2

Table 2 comparison of formulation without disintegrant

| | absolute hardness [N/mm$^2$] | | | oral disintegration time [sec] | |
|---|---|---|---|---|---|
| | before humidification | after humidification | hardness retention rate [%] | before humidification | after humidification |
| Comp. Ex. 1-1 | 6.9 | 4.1 | 59 | 72 | not less than 120 |
| Comp. Ex. 1-2 | 6.7 | 3.7 | 55 | 46 | not less than 120 |

TABLE 2-continued

Table 2 comparison of formulation without disintegrant

|  | absolute hardness [N/mm$^2$] | | hardness retention rate [%] | oral disintegration time [sec] | |
|---|---|---|---|---|---|
|  | before humidification | after humidification |  | before humidification | after humidification |
| Comp. Ex. 1-3 | 6.5 | 3.6 | 55 | 24 | not less than 120 |
| Comp. Ex. 1-4 | 5.7 | 3.3 | 58 | 24 | 117 |
| Comp. Ex. 1-5 | 4.7 | 3.1 | 66 | 20 | 110 |
| Comp. Ex. 1-6 | 3.9 | 2.0 | 51 | 20 | 110 |
| Comp. Ex. 1-7 | 2.8 | 1.4 | 50 | 19 | not less than 120 |

Example 1 and Comparative Example 2

Kind of Disintegrant (1)

Crystalline cellulose (CEOLUS PH-101), anhydrous calcium hydrogen phosphate and each disintegrant were mixed at the ratios shown in Table 3, magnesium stearate was added to the mixed powder and they were further admixed. The obtained mixture was applied to an oil hydraulic press to give tablets (tableting conditions: tableting pressure 6 kN, 120 mg/tablet, diameter 7 mm, round shape with beveled edge).

As the disintegrant, corn starch, crospovidone (KollidonCL: manufactured by BASF Japan), carmellose, sodium carboxymethyl starch (EXPLOTAB: manufactured by Kimura Sangyo Co., Ltd.), croscarmellose sodium (Ac-Di-Sol: manufactured by GOKYO TRADING CO., LTD.), carmellose calcium (ECG-505: manufactured by GOTOKU CHEMICAL COMPANY LTD.), and low-substituted hydroxypropylcellulose (LH-11: manufactured by Shin-Etsu Chemical Co., Ltd.) were used.

TABLE 3

Table 3 Kind of disintegrant formulation ratio (wt %)

| component | | Ex. 1 | Comp. Ex. 2-1 | Comp. Ex. 2-2 | Comp. Ex. 2-3 | Comp. Ex. 2-4 | Comp. Ex. 2-5 | Comp. Ex. 2-6 |
|---|---|---|---|---|---|---|---|---|
| crystalline cellulose | | 35.7 | 35.7 | 35.7 | 35.7 | 35.7 | 35.7 | 35.7 |
| anhydrous calcium hydrogen phosphate | | 53.5 | 53.5 | 53.5 | 53.5 | 53.5 | 53.5 | 53.5 |
| various disintegrants | corn starch | 10.0 | — | — | — | — | — | — |
| | crospovidone | — | 10.0 | — | — | — | — | — |
| | carmellose | — | — | 10.0 | — | — | — | — |
| | sodium carboxymethyl starch | — | — | — | 10.0 | — | — | — |
| | croscarmellose sodium | — | — | — | — | 10.0 | — | — |
| | carmellose calcium | — | — | — | — | — | 10.0 | — |
| | low-substituted hydroxypropylcellulose | — | — | — | — | — | — | 10.0 |
| magnesium stearate | | 0.8 | 0.8 | 0.8 | 0.8 | 0.8 | 0.8 | 0.8 |
| total | | 100.0 | 100.0 | 100.0 | 100.0 | 100.0 | 100.0 | 100.0 |

Using the obtained tablets, the tablet hardness and oral disintegration time were measured before and after humidification under 40° C. relative humidity 75% conditions for 3 days. The obtained results are shown in Table 4.

When corn starch was added as a disintegrant, absolute hardness of 1.0 N/mm$^2$ or above and oral disintegration time of within 30 seconds were maintained before and after humidification, and hardness retention rate could be kept as high as not less than 50% (Example 1).

On the other hand, when other disintegrant was used, none of them satisfied all criteria of absolute hardness of 1.0 N/mm$^2$ or above before and after humidification, oral disintegration time before and after humidification of within 30 seconds, and hardness retention rate of not less than 50%.

TABLE 4

Comparison of kind of disintegrant

| | absolute hardness [N/mm$^2$] | | hardness retention rate [%] | oral disintegration time [sec] | |
|---|---|---|---|---|---|
| | before humidification | after humidification | | before humidification | after humidification |
| Ex. 1 (corn starch) | 4.8 | 2.9 | 60 | 11 | 20 |
| Comp. Ex. 2-1 (crospovidone) | 4.0 | 1.2 | 30 | 10 | 16 |
| Comp. Ex. 2-2 (carmellose) | 4.6 | 1.8 | 39 | 7 | 12 |
| Comp. Ex. 2-3 (sodium carboxymethyl starch) | 3.2 | 1.5 | 47 | 20 | 60 |
| Comp. Ex. 2-4 (croscarmellose sodium) | 4.7 | 2.2 | 47 | 42 | 60 |
| Comp. Ex. 2-5 (carmellose calcium) | 4.4 | 2.2 | 50 | 9 | 39 |
| Comp. Ex. 2-6 (low-substituted hydroxypropylcellulose) | 5.6 | 3.1 | 55 | 12 | 31 |

Example 2 and Comparative Example 3

Kind of Disintegrant (2)

Crystalline cellulose (CEOLUS PH-101), anhydrous calcium hydrogen phosphate and each disintegrant were mixed at the ratios shown in Table 5, magnesium stearate was added to the mixed powder and they were further admixed. The obtained mixture was applied to an oil hydraulic press to give tablets (tableting conditions: tableting pressure 6 kN, 120 mg/tablet, diameter 7 mm, round shape with beveled edge).

As the disintegrant, corn starch and carmellose were used. For comparison, a tablet without a disintegrant was also prepared in the same manner.

TABLE 5

Effect of corn starch formulation ratio (wt %)

| component | Ex. 2 | Comp. Ex. 3-1 | Comp. Ex. 3-2 |
|---|---|---|---|
| crystalline cellulose | 36.0 | 36.0 | 40.0 |
| anhydrous calcium hydrogen phosphate | 53.9 | 53.9 | 59.9 |
| corn starch | 10.0 | — | — |
| carmellose | — | 10.0 | — |
| magnesium stearate | 0.1 | 0.1 | 0.1 |
| total | 100.0 | 100.0 | 100.0 |

Using the obtained tablets, the tablet hardness and oral disintegration time were measured before and after humidification for a given period under 40° C. relative humidity 75% conditions. The obtained results are shown in Table 6.

When corn starch was added, the tablet was good even after 14 days of humidification, since the absolute hardness was 1.0 N/mm$^2$ or above, the oral disintegration time of within 30 seconds were maintained, and the hardness retention rate was not less than 50%.

On the other hand, when carmellose was added, hardness retention rate was already below 50% at 3 days after humidification, and humidification greatly affected the tablet property. When humidification preservation was extended to 14 days, the hardness retention rate decreased to 40%. At this stage, slight concave and convex was observed on the tablet surface. When a disintegrant was not added, oral disintegration time was prolonged as the humidification period is extended, and the oral disintegration time was markedly slow and was 115 seconds at 14 days after humidification.

The orally disintegrating tablet of the present invention using a natural starch as a disintegrant is superior to orally disintegrating tablets using carmellose as a disintegrant, since it maintains the hardness after preservation under humidification conditions.

TABLE 6

Comparison of effect of corn starch (storage conditions: 40° C. relative humidity 75%)

| | humidification preservation period | absolute hardness [N/mm²] | | hardness retention rate [%] | oral disintegration time [seconds] | |
|---|---|---|---|---|---|---|
| | | before humidification | after humidification | | before humidification | after humidification |
| Ex. 2 | 3 days | 6.3 | 4.3 | 68 | 11 | 16 |
| (corn starch) | 7 days | | 4.6 | 73 | | 16 |
| | 14 days | | 4.2 | 67 | | 16 |
| Comp. Ex. 3-1 | 3 days | 6.7 | 3.2 | 48 | 10 | 12 |
| (carmellose) | 14 days | | 2.7 | 40 | | 26 |
| Comp. Ex. 3-2 | 3 days | 6.2 | 4.1 | 66 | 19 | 24 |
| (no | 7 days | | 4.6 | 74 | | 38 |
| disintegrant) | 14 days | | 4.0 | 65 | | 115 |

In dispensing pharmacy and the like, humidity change is assumed between within and after business hours. Therefore, the tablets produced in Example 2 and Comparative Example 3-1 were cyclic-stored at 25° C. (2 repeats of a cycle of 3 days at relative humidity 75%, then one day at relative humidity 11%). The tablet hardness and oral disintegration time before and after preservation were measured. The obtained results are shown in Table 7.

When corn starch was added, the hardness retention rate was 95%, showing almost no decrease in the hardness. In contrast when carmellose was added, the hardness decreased by not less than 30%.

TABLE 7

Comparison of effect of corn starch (25° C. cyclic storage)

| | absolute hardness [N/mm²] | | hardness retention rate [%] | oral disintegration time [seconds] | |
|---|---|---|---|---|---|
| | before humidification | after humidification | | before humidification | after humidification |
| Ex. 2 (corn-starch) | 6.3 | 6.0 | 95 | 11 | 10 |
| Comp. Ex. 3-1 (carmellose) | 6.7 | 4.5 | 67 | 10 | 11 | cyclic storage conditions:
25° C. relative humidity 75% 3 days→25° C. relative humidity 11% one day→25° C. relative humidity 75% 3 days→25° C. relative humidity 11% one day From the above results, it has been clarified that, with the addition of corn starch, the hardness of the level almost before humidification can be restored when a low humidity environment is produced again after exposure to a humidification environment in clinical setting.

Example 3 and Comparative Example 4

Kind of Natural Starches

Crystalline cellulose (CEOLUS PH-101), anhydrous calcium hydrogen phosphate and each starch were mixed at the ratios shown in Table 8, magnesium stearate was added to the mixed powder and they were further admixed. The obtained mixture was applied to an oil hydraulic press to give tablets (tableting conditions: tableting pressure potato starch (4 kN), other than potato starch (6 kN), 120 mg/tablet, diameter 7 mm, round shape with beveled edge).

As the starch, corn starch, wheat starch (Matsutani Kiku: manufactured by Matsutani Chemical Industry Co., Ltd.), rice starch (nonglutinous rice starch: manufactured by Shimada Kagaku Kokyo), potato starch (Matsutani Himawari: manufactured by Matsutani Chemical Industry Co., Ltd.), pregelatinized starch (AMICOL C: manufactured by NIPPON STARCH CHEMICAL CO., LTD.), partly pregelatinized starch (starch 1500: manufactured by Japan Colorcon Ltd.) were used.

TABLE 8

Kind of natural starches formulation ratio (wt %)

| component | | Ex. 3-1 | Ex. 3-2 | Ex. 3-3 | Ex. 3-4 | Comp. Ex. 4-1 | Comp. Ex. 4-2 |
|---|---|---|---|---|---|---|---|
| crystalline cellulose | | 35.7 | 35.7 | 35.7 | 35.7 | 35.7 | 35.7 |
| anhydrous calcium hydrogen phosphate | | 53.5 | 53.5 | 53.5 | 53.5 | 53.5 | 53.5 |
| natural starches | corn starch | 10.0 | — | — | — | — | — |
| | wheat starch | — | 10.0 | — | — | — | — |
| | rice starch | — | — | 10.0 | — | — | — |
| | potato starch | — | — | — | 10.0 | — | — |
| pregelatinized starch (AMICOL C) | | — | — | — | — | 10.0 | — |
| partly pregelatinized starch (starch 1500) | | — | — | — | — | — | 10.0 |
| magnesium stearate | | 0.8 | 0.8 | 0.8 | 0.8 | 0.8 | 0.8 |
| total | | 100.0 | 100.0 | 100.0 | 100.0 | 100.0 | 100.0 |

Using the obtained tablets, the tablet hardness and oral disintegration time were measured before and after humidification under 40° C. relative humidity 75% conditions for 3 days. The obtained results are shown in Table 9. When wheat starch, rice starch and potato starch were added as the disintegrant, the criteria of absolute hardness before and after humidification of 1.0 N/mm$^2$ or above and oral disintegration time before and after humidification of within 30 seconds, and hardness retention rate of not less than 50% were met, and effects similar to those of corn starch were exhibited.

On the other hand, when processed starch such as AMICOL C and starch 1500 was added, delayed disintegration after humidification could not be suppressed and the oral disintegration time exceeded 30 seconds.

TABLE 9

Comparison of kind of natural starches

| | absolute hardness [N/mm$^2$] | | hardness retention rate [%] | oral disintegration time [seconds] | |
|---|---|---|---|---|---|
| | before humidification | after humidification | | before humidification | after humidification |
| Ex. 3-1 (corn starch) | 4.8 | 2.9 | 60 | 11 | 20 |
| Ex. 3-2 (wheat starch) | 5.3 | 3.1 | 58 | 12 | 22 |
| Ex. 3-3 (rice starch) | 6.7 | 4.3 | 64 | 15 | 30 |
| Ex. 3-4 (potato starch) | 3.3 | 2.0 | 61 | 12 | 20 |
| Comp. Ex. 4-1 (pregelatinized starch (AMICOL C)) | 5.4 | 3.0 | 56 | 35 | not less than 120 |
| Comp. Ex. 4-2 (partly pregelatinized starch (starch 1500)) | 4.7 | 2.4 | 51 | 18 | 95 |

Example 4

Kind of Crystalline Cellulose

Various crystalline celluloses, anhydrous calcium hydrogen phosphate and corn starch were mixed at the ratios shown in Table 10, magnesium stearate was added to the mixed powder and they were further admixed. The obtained mixture was applied to an oil hydraulic press to give tablets (tableting conditions: tableting pressure CEOLUS KG-802 and PH-F20J (4 kN), other than CEOLUS KG-802 and PH-F20J (6 kN), 120 mg/tablet, diameter 7 mm, round shape with beveled edge).

TABLE 10

| | Kind of crystalline cellulose formulation ratio (wt %) | | | | | | |
|---|---|---|---|---|---|---|---|
| component | | Ex. 4-1 | Ex. 4-2 | Ex. 4-3 | Ex. 4-4 | Ex. 4-5 | Ex. 4-5 |
| crystalline cellulose bulk density (trade name) | 0.21 g/cm$^3$ (CEOLUS KG-802) | 35.7 | — | — | — | — | — |
| | 0.23 g/cm$^3$ (CEOLUS PH-F20J) | — | 35.7 | — | — | — | — |
| | 0.29 g/cm$^3$ (CEOLUS PH-101) | — | — | 35.7 | — | — | — |
| | 0.30 g/cm$^3$ (CEOLUS PH-102) | — | — | — | 35.7 | — | — |
| | 0.41 g/cm$^3$ (CEOLUS PH-301) | — | — | — | — | 35.7 | — |
| | 0.43 g/cm$^3$ (CEOLUS PH-302) | — | — | — | — | — | 35.7 |
| anhydrous calcium hydrogen phosphate | | 53.5 | 53.5 | 53.5 | 53.5 | 53.5 | 53.5 |
| corn starch | | 10.0 | 10.0 | 10.0 | 10.0 | 10.0 | 10.0 |
| magnesium stearate | | 0.8 | 0.8 | 0.8 | 0.8 | 0.8 | 0.8 |
| total | | 100.0 | 100.0 | 100.0 | 100.0 | 100.0 | 100.0 |

Using the obtained tablets, the tablet hardness and oral disintegration time were measured before and after humidification under 40° C. relative humidity 75% conditions for 3 days. The obtained results are shown in Table 11. Any crystalline cellulose used satisfied the conditions of absolute hardness before and after humidification of 1.0 N/mm$^2$ or above, and oral disintegration time before and after humidification of within 30 seconds, and the hardness retention rate of not less than 50%. From the aspects of oral disintegration time after humidification, CEOLUS PH-101 (0.29 g/cm$^3$), CEOLUS PH-102 (0.30 g/cm$^3$), CEOLUS PH-301 (0.41 g/cm$^3$) and CEOLUS PH-302 (0.43 g/cm$^3$) are preferable, and the bulk density of crystalline cellulose was 0.29-0.43 g/cm$^3$.

TABLE 11

| | Comparison of kind of crystalline cellulose | | | | |
|---|---|---|---|---|---|
| | absolute hardness [N/mm$^2$] | | hardness retention rate [%] | oral disintegration time [seconds] | |
| | before humidification | after humidification | | before humidification | after humidification |
| Ex. 4-1 (0.21 g/cm$^3$) | 4.1 | 2.5 | 61 | 14 | 25 |
| Ex. 4-2 (0.23 g/cm$^3$) | 4.2 | 2.8 | 67 | 18 | 28 |
| Ex. 4-3 (0.29 g/cm$^3$) | 4.8 | 2.9 | 60 | 11 | 20 |

TABLE 11-continued

Comparison of kind of crystalline cellulose

| | absolute hardness [N/mm$^2$] | | | oral disintegration time [seconds] | |
|---|---|---|---|---|---|
| | before humidification | after humidification | hardness retention rate [%] | before humidification | after humidification |
| Ex. 4-4 (0.30 g/cm$^3$) | 5.0 | 3.2 | 64 | 11 | 20 |
| Ex. 4-5 (0.41 g/cm$^3$) | 4.1 | 2.8 | 68 | 9 | 16 |
| Ex. 4-6 (0.43 g/cm$^3$) | 4.0 | 2.6 | 65 | 12 | 16 |

The numbers in parentheses show bulk density of crystalline cellulose.

Example 5

Kind of Lubricant

Crystalline cellulose (CEOLUS PH-101), anhydrous calcium hydrogen phosphate and corn starch were mixed at the ratios shown in Table 12, a lubricant was added to the mixed powder and they were further admixed. The obtained mixture was applied to an oil hydraulic press to give a tablet (120% mg/tablet, diameter 7 mm, round shape with beveled edge) at a tableting pressure of 6 kN. As the lubricant, stearic acid (stearic acid A: manufactured by Nippon Fine Chemical), calcium stearate (manufactured by Taihei Chemical Industrial Co., Ltd.), sodium stearyl fumarate (PRUV: manufactured by Kimura Sangyo Co., Ltd.), talc (manufactured by Hayashi-Kasei Co., Ltd.), light anhydrous silicic acid (AEROSIL 200: manufactured by NIPPON AEROSIL) were used.

TABLE 12

Kind of lubricant formulation ratio (wt %)

| component | | Ex. 5-1 | Ex. 5-2 | Ex. 5-3 | Ex. 5-4 | Ex. 5-5 |
|---|---|---|---|---|---|---|
| crystalline cellulose | | 35.7 | 35.7 | 35.7 | 35.7 | 35.9 |
| anhydrous calcium hydrogen phosphate | | 53.5 | 53.5 | 53.5 | 53.5 | 53.8 |
| corn starch | | 10.0 | 10.0 | 10.0 | 10.0 | 10.0 |
| various lubricants | stearic acid | 0.8 | — | — | — | — |
| | calcium stearate | — | 0.8 | — | — | — |
| | sodium stearyl fumarate | — | — | 0.8 | — | — |
| | talc | — | — | — | 0.8 | — |
| | light anhydrous silicic acid | — | — | — | — | 0.3 |
| total | | 100.0 | 100.0 | 100.0 | 100.0 | 100.0 |

Using the obtained tablets, the tablet hardness and oral disintegration time were measured before and after humidification under 40° C. relative humidity 75% conditions for 3 days. The obtained results are shown in Table 13. With any lubricant, all the criteria of the absolute hardness before and after humidification and oral disintegration time before and after humidification, and the hardness retention rate were met, and similar effects were exhibited irrespective of the kind of lubricant.

TABLE 13

Comparison kind of lubricant

| | absolute hardness [N/mm$^2$] | | | oral disintegration time [seconds] | |
|---|---|---|---|---|---|
| | before humidification | after humidification | hardness retention rate [%] | before humidification | after humidification |
| Ex. 5-1 (stearic acid) | 5.5 | 4.0 | 73 | 15 | 21 |

TABLE 13-continued

Comparison kind of lubricant

| | absolute hardness [N/mm$^2$] | | | oral disintegration time [seconds] | |
|---|---|---|---|---|---|
| | before humidification | after humidification | hardness retention rate [%] | before humidification | after humidification |
| Ex. 5-2 (calcium stearate) | 5.2 | 3.7 | 71 | 13 | 16 |
| Ex. 5-3 (sodium stearyl fumarate) | 6.4 | 4.0 | 63 | 10 | 14 |
| Ex. 5-4 (talc) | 7.0 | 4.6 | 66 | 16 | 5 |
| Ex. 5-5 (light anhydrous silicic acid) | 6.6 | 4.0 | 61 | 5 | 7 |

Example 6 and Comparative Example 5

Blending Ratio of Anhydrous Calcium Hydrogen Phosphate

Crystalline cellulose (CEOLUS PH-101), anhydrous calcium hydrogen phosphate and corn starch were mixed at the ratios shown in Table 14, magnesium stearate was added to the mixed powder and they were further admixed. The obtained mixture was applied to an oil hydraulic press to give a tablet (120 mg/tablet, diameter 7 mm, round shape with beveled edge) at a tableting pressure of 6 kN.

TABLE 14

Blending ratio of anhydrous calcium hydrogen phosphate formulation ratio (wt %)

| component | Comp. Ex. 5-1 | Ex. 6-1 | Ex. 6-2 | Ex. 6-3 | Comp. Ex. 5-2 | Comp. Ex. 5-3 |
|---|---|---|---|---|---|---|
| crystalline cellulose | 69.2 | 59.2 | 49.2 | 29.2 | 19.2 | 9.2 |
| anhydrous calcium hydrogen phosphate | 20.0 | 30.0 | 40.0 | 60.0 | 70.0 | 80.0 |
| corn starch | 10.0 | 10.0 | 10.0 | 10.0 | 10.0 | 10.0 |
| magnesium stearate | 0.8 | 0.8 | 0.8 | 0.8 | 0.8 | 0.8 |
| total | 100.0 | 100.0 | 100.0 | 100.0 | 100.0 | 100.0 |

Using the obtained tablets, the tablet hardness and oral disintegration time were measured before and after humidification under 40° C. relative humidity 75% conditions for 3 days. The obtained results are shown in Table 15.

When the blending ratio of anhydrous calcium hydrogen phosphate was 30-60 wt %, the criteria of the absolute hardness before and after humidification of 1.0 N/mm$^2$ or above and oral disintegration time before and after humidification of within 30 seconds, and the hardness retention rate of not less than 50% were met, and good tablet was obtained. When the blending ratio of anhydrous calcium hydrogen phosphate was 20 wt % and not less than 70 wt %, the absolute hardness after humidification and hardness retention rate satisfied the criteria, but oral disintegration time after humidification exceeded 30 seconds, thus failing to meet the criterion.

TABLE 15

Comparison of blending ratio of anhydrous calcium hydrogen phosphate

| | absolute hardness [N/mm$^2$] | | | oral disintegration time [seconds] | |
|---|---|---|---|---|---|
| | before humidification | after humidification | hardness retention rate [%] | before humidification | after humidification |
| Comp. Ex. 5-1 (20 wt %) | 6.9 | 4.5 | 65 | 18 | 33 |
| Ex. 6-1 (30 wt %) | 6.4 | 4.3 | 67 | 19 | 27 |
| Ex. 6-2 (40 wt %) | 5.0 | 3.9 | 78 | 10 | 21 |

TABLE 15-continued

Comparison of blending ratio of anhydrous calcium hydrogen phosphate

|  | absolute hardness [N/mm$^2$] | | | oral disintegration time [seconds] | |
| --- | --- | --- | --- | --- | --- |
|  | before humidification | after humidification | hardness retention rate [%] | before humidification | after humidification |
| Ex. 6-3 (60 wt %) | 3.8 | 3.0 | 79 | 10 | 29 |
| Comp. Ex. 5-2 (70 wt %) | 3.9 | 2.4 | 62 | 8 | 33 |
| Comp. Ex. 5-3 (80 wt %) | 2.5 | 1.5 | 60 | 5 | 50 |

The numbers in parentheses show blending ratio of anhydrous calcium hydrogen phosphate.

Example 7 and Comparative Example 6

Blending Ratio of Corn Starch

Ethenzamide as an efficacy ingredient, crystalline cellulose (CEOLUS PH-101), anhydrous calcium hydrogen phosphate and corn starch were mixed at the ratios shown in Table 16, magnesium stearate was added to the mixed powder and they were further admixed. The obtained mixture was applied to an oil hydraulic press to give a tablet (120 mg/tablet, diameter 7 mm, round shape with beveled edge). The tableting pressure was 4 kN when the blending ratio of corn starch was 1-3 wt %, 6 kN when the blending ratio of corn starch was 5-20 wt %, and 10 kN when the blending ratio of corn starch was 25-40 wt %.

TABLE 16

Blending ratio of corn starch formulation ratio (wt %)

| component | Comp. Ex. 6-1 | Comp. Ex. 6-2 | Ex. 7-1 | Ex. 7-2 | Ex. 7-3 | Ex. 7-4 | Ex. 7-5 | Ex. 7-6 | Ex. 7-7 |
| --- | --- | --- | --- | --- | --- | --- | --- | --- | --- |
| ethenzamide | 5.0 | 5.0 | 5.0 | 5.0 | 5.0 | 5.0 | 5.0 | 5.0 | 5.0 |
| crystalline cellulose | 55.2 | 54.2 | 53.2 | 51.2 | 46.2 | 36.2 | 31.2 | 26.2 | 16.2 |
| anhydrous calcium hydrogen phosphate | 38.0 | 38.0 | 38.0 | 38.0 | 38.0 | 38.0 | 38.0 | 38.0 | 38.0 |
| corn starch | 1.0 | 2.0 | 3.0 | 5.0 | 10.0 | 20.0 | 25.0 | 30.0 | 40.0 |
| magnesium stearate | 0.8 | 0.8 | 0.8 | 0.8 | 0.8 | 0.8 | 0.8 | 0.8 | 0.8 |
| total | 100.0 | 100.0 | 100.0 | 100.0 | 100.0 | 100.0 | 100.0 | 100.0 | 100.0 |

Using the obtained tablets, the tablet hardness and oral disintegration time were measured before and after humidification under 40° C. relative humidity 75% conditions for 3 days. The obtained results are shown in Table 17.

When the blending ratio of corn starch was 3-40 wt % of the tablet, the criteria of the absolute hardness before and after humidification of 1.0 N/mm$^2$ or above and oral disintegration time before and after humidification of within 30 seconds, and the hardness retention rate of not less than 50% were met, and good tablet was obtained. When the blending ratio of corn starch was 2 wt % or below, the oral disintegration time after humidification exceeded 30 seconds, thus failing to meet the criterion.

TABLE 17

Comparison of blending ratio of corn starch

|  | absolute hardness [N/mm$^2$] | | | oral disintegration time [seconds] | |
| --- | --- | --- | --- | --- | --- |
|  | before humidification | after humidification | hardness retention rate [%] | before humidification | after humidification |
| Comp. Ex. 6-1 (1 wt %) | 4.3 | 2.8 | 65 | 20 | 42 |

TABLE 17-continued

Comparison of blending ratio of corn starch

| | absolute hardness [N/mm²] | | | oral disintegration time [seconds] | |
| --- | --- | --- | --- | --- | --- |
| | before humidification | after humidification | hardness retention rate [%] | before humidification | after humidification |
| Comp. Ex. 6-2 (2 wt %) | 4.5 | 2.9 | 64 | 15 | 36 |
| Ex. 7-1 (3 wt %) | 4.2 | 2.8 | 67 | 15 | 21 |
| Ex. 7-2 (5 wt %) | 5.1 | 3.3 | 65 | 16 | 27 |
| Ex. 7-3 (10 wt %) | 5.0 | 3.3 | 66 | 12 | 18 |
| Ex. 7-4 (20 wt %) | 3.9 | 2.2 | 56 | 11 | 10 |
| Ex. 7-5 (25 wt %) | 5.2 | 3.6 | 69 | 12 | 8 |
| Ex. 7-6 (30 wt %) | 5.0 | 3.2 | 64 | 8 | 8 |
| Ex. 7-7 (40 wt %) | 3.1 | 1.7 | 55 | 9 | 9 |

The numbers in parentheses show blending ratio of corn starch.

Example 8 and Comparative Example 7

Amount of Lubricant

Crystalline cellulose (CEOLUS PH-101), anhydrous calcium hydrogen phosphate and corn starch were mixed at the ratios shown in Table 18, magnesium stearate was added to the mixed powder and they were further admixed. The obtained mixture was applied to an oil hydraulic press to give a tablet (120-122 mg/tablet, diameter 7 mm, round shape with beveled edge) at a tableting pressure of 6 kN.

TABLE 18

Blending ratio of magnesium stearate formulation ratio (wt %)

| component | Ex. 8-1 | Ex. 8-2 | Ex. 8-3 | Ex. 8-4 | Ex. 8-5 | Ex. 8-6 | Ex. 8-7 | Comp. Ex. 7-1 | Comp. Ex. 7-2 |
| --- | --- | --- | --- | --- | --- | --- | --- | --- | --- |
| crystalline cellulose | 36.0 | 36.0 | 35.8 | 35.7 | 35.6 | 35.4 | 35.3 | 35.2 | 34.9 |
| anhydrous calcium hydrogen phosphate | 54.0 | 53.9 | 53.7 | 53.5 | 53.4 | 53.0 | 52.9 | 52.9 | 52.4 |
| corn starch | 10.0 | 10.0 | 10.0 | 10.0 | 10.0 | 10.0 | 10.0 | 9.9 | 9.8 |
| magnesium stearate | 0.01 | 0.1 | 0.5 | 0.8 | 1.0 | 1.6 | 1.8 | 2.0 | 2.9 |
| total | 100.0 | 100.0 | 100.0 | 100.0 | 100.0 | 100.0 | 100.0 | 100.0 | 100.0 |
| weight (mg) per tablet | 120 | 120 | 121 | 120 | 120 | 120 | 120 | 121 | 122 |

Using the obtained tablets, the tablet hardness and oral disintegration time were measured before and after humidification under 40° C. relative humidity 75% conditions for 3 days. The obtained results are shown in Table 19.

When the blending ratio of magnesium stearate increased, the disintegration time after humidification was particularly prolonged. When the blending ratio of magnesium stearate was 0.01-1.8 wt %, the criteria of the absolute hardness before and after humidification of 1.0 N/mm² or above and oral disintegration time before and after humidification of within 30 seconds, and the hardness retention rate of not less than 50% were met, and good tablet was obtained. When the blending ratio of magnesium stearate was 2 wt % or above, the hardness after humidification slightly decreased, the disintegration time after humidification was prolonged, and the oral disintegration time exceeded 30 seconds.

TABLE 19

Comparison of blending ratio of magnesium stearate

| | absolute hardness [N/mm²] | | hardness retention rate [%] | oral disintegration time [seconds] | |
|---|---|---|---|---|---|
| | before humidification | after humidification | | before humidification | after humidification |
| Ex. 8-1 (0.01 wt %) | 6.4 | 4.2 | 66 | 10 | 8 |
| Ex. 8-2 (0.1 wt %) | 6.3 | 4.3 | 68 | 11 | 16 |
| Ex. 8-3 (0.5 wt %) | 5.0 | 3.6 | 72 | 14 | 15 |
| Ex. 8-4 (0.8 wt %) | 4.8 | 2.9 | 60 | 11 | 20 |
| Ex. 8-5 (1 wt %) | 4.5 | 2.8 | 62 | 15 | 18 |
| Ex. 8-6 (1.6 wt %) | 4.8 | 2.7 | 56 | 14 | 23 |
| Ex. 8-7 (1.8 wt %) | 4.5 | 2.4 | 53 | 15 | 29 |
| Comp. Ex. 7-1 (2 wt %) | 3.7 | 2.2 | 59 | 23 | 35 |
| Comp. Ex. 7-2 (2.9 wt %) | 3.1 | 2.0 | 65 | 26 | 62 |

The numbers in parentheses show blending ratio of magnesium stearate.

Example 9 and Comparative Example 8

Blending Ratio of Efficacy Ingredient (1)

Ethenzamide, crystalline cellulose (CEOLUS PH-101), anhydrous calcium hydrogen phosphate and corn starch were mixed at the ratios shown in Table 20, magnesium stearate was added to the mixed powder and they were further admixed. The obtained mixture was applied to an oil hydraulic press to give a tablet (120 mg/tablet, diameter 7 mm, round shape with beveled edge). The tableting pressure was 6 kN when the blending ratio of ethenzamide was 0.01-50 wt %, and 4 kN when the blending ratio of ethenzamide was not less than 60 wt %.

The formulation ratios of the components other than the efficacy ingredient were set the same and that of the efficacy ingredient was changed from 0.01 to 70 wt %.

TABLE 20

Blending ratio of efficacy ingredient formulation ratio (wt %)

| component | Ex. 9-1 | Ex. 9-2 | Ex. 9-3 | Ex. 9-4 | Ex. 9-5 | Comp. Ex. 8-1 |
|---|---|---|---|---|---|---|
| ethenzamide | 0.01 | 10.00 | 25.00 | 50.00 | 60.00 | 70.00 |
| crystalline cellulose | 49.19 | 44.28 | 36.90 | 24.60 | 19.68 | 14.76 |
| anhydrous calcium hydrogen phosphate | 40.00 | 36.00 | 30.00 | 20.00 | 16.00 | 12.00 |

TABLE 20-continued

Blending ratio of efficacy ingredient formulation ratio (wt %)

| component | Ex. 9-1 | Ex. 9-2 | Ex. 9-3 | Ex. 9-4 | Ex. 9-5 | Comp. Ex. 8-1 |
|---|---|---|---|---|---|---|
| corn starch | 10.00 | 9.00 | 7.50 | 5.00 | 4.00 | 3.00 |
| magnesium stearate | 0.80 | 0.72 | 0.60 | 0.40 | 0.32 | 0.24 |
| total | 100.00 | 100.00 | 100.00 | 100.00 | 100.00 | 100.00 |

Using the obtained tablets, the tablet hardness and oral disintegration time were measured before and after humidification under 40° C. relative humidity 75% conditions for 3 days. The obtained results are shown in Table 21.

When the blending ratio of ethenzamide was 0.01-60 wt %, the criteria of the absolute hardness before and after humidification of 1.0 N/mm² or above and oral disintegration time before and after humidification of within 30 seconds, and the hardness retention rate of not less than 50% were met, and good tablet was obtained. When the blending ratio of ethenzamide was not less than 70 wt %, the oral disintegration time after humidification exceeded 30 seconds, thus failing to meet the criterion.

From the above results, it was confirmed that the effect of the invention can be exhibited even when the efficacy ingredient ethenzamide was added in 60 wt % of the total weight of the tablet.

TABLE 21

Comparison of blending ratio of efficacy ingredient

| | absolute hardness [N/mm$^2$] | | | oral disintegration time [seconds] | |
|---|---|---|---|---|---|
| | before humidification | after humidification | hardness retention rate [%] | before humidification | after humidification |
| Ex. 9-1 (0.01 wt %) | 5.4 | 3.6 | 67 | 14 | 25 |
| Ex. 9-2 (10 wt %) | 5.2 | 3.3 | 63 | 14 | 24 |
| Ex. 9-3 (25 wt %) | 4.8 | 3.5 | 73 | 15 | 24 |
| Ex. 9-4 (50 wt %) | 4.3 | 3.8 | 88 | 15 | 26 |
| Ex. 9-5 (60 wt %) | 2.8 | 2.4 | 86 | 13 | 28 |
| Comp. Ex. 8-1 (70 wt %) | 2.5 | 2.5 | 100 | 20 | 65 |

The numbers in parentheses show blending ratio of ethenzamide.

Example 10 and Comparative Example 9

Blending Ratio of Efficacy Ingredient (2)

Ethenzamide, crystalline cellulose (CEOLUS PH-101), anhydrous calcium hydrogen phosphate and corn starch were mixed at the ratios shown in Table 22, magnesium stearate was added to the mixed powder and they were further admixed. The obtained mixture was applied to an oil hydraulic press to give a tablet (120 mg/tablet, diameter 7 mm, round shape with beveled edge) at a tableting pressure of 6 kN.

The blending ratio of anhydrous calcium hydrogen phosphate was 40 wt % of the total amount of the tablet components other than the efficacy ingredient.

TABLE 22

Blending ratio of efficacy ingredient formulation ratio (wt %)

| component | Ex. 10-1 | Ex. 10-2 | Ex. 10-3 | Ex. 10-4 | Ex. 10-5 | Comp. Ex. 9-1 |
|---|---|---|---|---|---|---|
| ethenzamide | 0.0 | 5.0 | 10.0 | 25.0 | 50.0 | 70.0 |
| crystalline cellulose | 49.2 | 46.2 | 43.2 | 34.2 | 19.2 | 7.2 |
| anhydrous calcium hydrogen phosphate | 40.0 | 38.0 | 36.0 | 30.0 | 20.0 | 12.0 |

TABLE 22-continued

Blending ratio of efficacy ingredient formulation ratio (wt %)

| component | Ex. 10-1 | Ex. 10-2 | Ex. 10-3 | Ex. 10-4 | Ex. 10-5 | Comp. Ex. 9-1 |
|---|---|---|---|---|---|---|
| corn starch | 10.0 | 10.0 | 10.0 | 10.0 | 10.0 | 10.0 |
| magnesium stearate | 0.8 | 0.8 | 0.8 | 0.8 | 0.8 | 0.8 |
| total | 100.0 | 100.0 | 100.0 | 100.0 | 100.0 | 100.0 |

Using the obtained tablets, the tablet hardness and oral disintegration time were measured before and after humidification under 40° C. relative humidity 75% conditions for 3 days. The obtained results are shown in Table 23.

When the blending ratio of ethenzamide was 0-50 wt %, the criteria of the absolute hardness before and after humidification of 1.0 N/mm$^2$ or above and oral disintegration time before and after humidification of within 30 seconds, and the hardness retention rate of not less than 50% were met, and good tablet was obtained. When the blending ratio of ethenzamide was not less than 70 wt %, the oral disintegration time after humidification exceeded 30 seconds, thus failing to meet the criterion.

From the above results, it was confirmed that the effect of the invention can be exhibited even when the efficacy ingredient ethenzamide was added in 50 wt % of the total weight of the tablet.

In addition, the tablets before and after humidification of Examples 10-1-10-5 did not show roughness to the tongue and dryness, and had good palatability. Moreover, no change due to humidification was observed in the properties such as concave and convex of the tablet surface and the like.

TABLE 23

Comparison of blending ratio of efficacy ingredient

| | absolute hardness [N/mm$^2$] | | | oral disintegration time [seconds] | |
|---|---|---|---|---|---|
| | before humidification | after humidification | hardness retention rate [%] | before humidification | after humidification |
| Ex. 10-1 (0 wt %) | 5.0 | 3.9 | 78 | 10 | 21 |
| Ex. 10-2 (5 wt %) | 5.0 | 3.3 | 66 | 12 | 18 |
| Ex. 10-3 (10 wt %) | 5.0 | 3.1 | 62 | 12 | 19 |
| Ex. 10-4 (25 wt %) | 4.2 | 2.9 | 69 | 10 | 20 |
| Ex. 10-5 (50 wt %) | 3.6 | 2.9 | 81 | 10 | 28 |
| Comp. Ex. 9-1 (70 wt %) | 3.3 | 3.1 | 94 | 18 | 60 |

The numbers in parentheses show blending ratio of ethenzamide.

Example 11

Kind of Efficacy Ingredient

An efficacy ingredient, crystalline cellulose, anhydrous calcium hydrogen phosphate and corn starch were mixed at the ratios shown in Table 24, magnesium stearate was added to the mixed powder and they were further admixed. The obtained mixture was applied to an oil hydraulic press to give a tablet (120 mg/tablet, diameter 7 mm, round shape with beveled edge). The tableting pressure was 15 kN for acetaminophen, and 6 kN for those other than acetaminophen. As the efficacy ingredient, mosapride citrate dihydrate (manufactured by Dainippon Sumitomo Pharma Co., Ltd.), ascorbic acid (manufactured by NACALAI TESQUE, INC.), indomethacin pulverized product (manufactured by Dainippon Sumitomo Pharma Co., Ltd.), and acetaminophen pulverized product (manufactured by Yamamoto-Kogyo: average particle size 17.7 μm) were used.

TABLE 24

Kind of efficacy ingredient formulation ratio (wt %)

| component | Ex. 11-1 | Ex. 11-2 | Ex. 11-3 | Ex. 11-4 |
|---|---|---|---|---|
| mosapride citrate dihydrate | 4.2 | — | — | — |
| ascorbic acid | — | 10.0 | — | — |
| indomethacin | — | — | 20.8 | — |
| acetaminophen | — | — | — | 50.0 |
| crystalline cellulose (CEOLUS PH-101) | 45.0 | 39.2 | — | 9.2 |
| crystalline cellulose (CEOLUS PH-102) | — | — | 28.4 | — |
| anhydrous calcium hydrogen phosphate (GS) | 40.0 | 40.0 | — | 30.0 |
| anhydrous calcium hydrogen phosphate (light) | — | — | 40.0 | — |
| corn starch | 10.0 | 10.0 | 10.0 | 10.0 |
| magnesium stearate | 0.8 | 0.8 | 0.8 | 0.8 |
| total | 100.0 | 100.0 | 100.0 | 100.0 |

Using the obtained tablets, the tablet hardness and oral disintegration time were measured before and after humidification under 40° C. relative humidity 75% conditions for 3 days. The obtained results are shown in Table 25.

When mosapride citrate dihydrate, ascorbic acid, indomethacin or acetaminophen was contained as an efficacy ingredient, the criteria of the absolute hardness before and after humidification of 1.0 N/mm$^2$ or above and oral disintegration time before and after humidification of within 30 seconds, and the hardness retention rate of not less than 50% were met, and good tablet was obtained.

From the above results, it was confirmed that the effect of the orally disintegrating tablet of the present invention can be exhibited irrespective of the kind of the efficacy ingredient.

TABLE 25

Comparison of kind of efficacy ingredient

| | absolute hardness [N/mm$^2$] | | | oral disintegration time [seconds] | |
|---|---|---|---|---|---|
| | before humidification | after humidification | hardness retention rate [%] | before humidification | after humidification |
| Ex. 11-1 (mosapride citrate dihydrate) | 5.4 | 3.5 | 65 | 14 | 18 |

TABLE 25-continued

Comparison of kind of efficacy ingredient

| | absolute hardness [N/mm$^2$] | | | oral disintegration time [seconds] | |
|---|---|---|---|---|---|
| | before humidification | after humidification | hardness retention rate [%] | before humidification | after humidification |
| Ex. 11-2 (ascorbic acid) | 3.5 | 2.2 | 63 | 14 | 22 |
| Ex. 11-3 (indomethacin) | 4.0 | 4.1 | 103 | 18 | 14 |
| Ex. 11-4 (acetaminophen) | 2.4 | 3.0 | 125 | 16 | 18 |

Example 12

Production of Efficacy Ingredient-Containing Particles

1) Acetaminophen-Containing Particles

Acetaminophen was coated to a coating amount of 10% to give acetaminophen-containing particles. The film components used were Aquacoat (manufactured by Asahi Kasei Chemicals Corporation), triacetine and mannitol at 100:25:50 wt %.

2) Mosapride Citrate-Containing Particles

Polysorbate 80 (The Japanese Pharmacopoeia polysorbate 80 (HX): manufactured by NOF CORPORATION, 31.5 g) was added to purified water (567 g), and they were sufficiently blended. Talc (manufactured by Hayashi-Kasei Co., Ltd., 73.5 g) and croscalmellose sodium (Ac-Di-Sol: manufactured by FMC BioPolymer, 52.5 g) were added, and the mixture was sufficiently stirred (1st fluid). Separately, sodium hydroxide was dissolved in purified water (67.65 g) and the solution was gradually added to methacrylic acid copolymer LD (POLYQUID PA-30S: manufactured by Sanyo Chemical Industries, Ltd., 705 g), and the mixture was stirred (2nd fluid). The 2nd fluid was suspended in the 1st fluid, and the suspension was sieved with a mesh with 177 μm pore diameter to give coating dispersion.

Mosapride citrate dihydrate (346.5 g) and light anhydrous silicic acid (AEROSIL 200: manufactured by NIPPON AEROSIL, 3.5 g) were sieved with a mesh with 500 μm pore diameter, and sufficiently mixed in a polyethylene bag to give a drug-containing composition. The composition was placed in a Wurster-fluidized bed granulator with a forced circulation device (improved Wurster-fluidized bed granulator, MP-01 SPC, manufactured by POWREX), and the above-mentioned coating dispersion was sprayed thereon. During spraying, the inlet air temperature was about 80-90° C., the outlet air temperature was about 26-30° C., and the production was performed while spraying the spray liquid from a bottom spray at a flow of 10-12 g/min, spray air flow of 80 L/min, spray air pressure of 0.2-0.3 MPa, side air pressure of 0.2-0.25 MPa, and inlet air flow of about 0.30-0.55 m$^3$/min. The coating was completed when the spray amount of coating dispersion was about 1306 g, and dried until the exhaustion temperature reached 42° C. The obtained particles were sieved with a 32 mesh (aperture 500 μm) sieve to give drug-containing particles having an average particle size of about 98 μm.

The efficacy ingredient-containing particles produced by the above-mentioned method, crystalline cellulose (CEOLUS PH-101), anhydrous calcium hydrogen phosphate and corn starch were mixed at the ratios shown in Table 26, magnesium stearate was added to the mixed powder and they were further admixed. The obtained mixture was applied to an oil hydraulic press to give a tablet (120 mg/tablet, diameter 7 mm, round shape with beveled edge) at a tableting pressure of 6 kN.

TABLE 26

Kind of efficacy ingredient formulation ratio (wt %)

| component | Ex. 12-1 | Ex. 12-2 |
|---|---|---|
| acetaminophen-containing particles | 11.0 | — |
| mosapride citrate-containing particles | — | 8.0 |
| crystalline cellulose (PH-101) | 38.2 | — |
| crystalline cellulose (PH-301) | — | 41.2 |
| anhydrous calcium hydrogen phosphate (GS) | 40.0 | — |
| anhydrous calcium hydrogen phosphate (heavy) | — | 40.0 |
| corn starch | 10.0 | 10.0 |
| magnesium stearate | 0.8 | 0.8 |
| total | 100.0 | 100.0 |

Using the obtained tablets, the tablet hardness and oral disintegration time were measured before and after humidification under 40° C. relative humidity 75% conditions for 3 days. The obtained results are shown in Table 27.

When the efficacy ingredient was mosapride citrate-containing particles or acetaminophen-containing particles, the criteria of the absolute hardness before and after humidification of 1.0 N/mm$^2$ or above and oral disintegration time before and after humidification of within 30 seconds, and the hardness retention rate of not less than 50% were met, and good tablet was obtained.

From the above results, it was confirmed that the effect of the composition for the orally disintegrating tablet of the present invention can be exhibited even when the efficacy ingredient-containing particles were used.

TABLE 27

Comparison of kind of efficacy ingredient

| | absolute hardness [N/mm$^2$] | | | oral disintegration time [seconds] | |
|---|---|---|---|---|---|
| | before humidification | after humidification | hardness retention rate [%] | before humidification | after humidification |
| Ex. 12-1 (acetaminophen-containing particles) | 3.5 | 2.3 | 66 | 13 | 18 |
| Ex. 12-2 (mosapride citrate-containing particles) | 4.4 | 3.1 | 70 | 12 | 9 |

INDUSTRIAL APPLICABILITY

The present invention provides an orally disintegrating tablet showing high tablet hardness and appropriate disintegration time not only before humidification but also after humidification.

This application is based on a patent application No. 2007-302284 filed in Japan, the contents of which are incorporated in full herein.

The invention claimed is:

1. An orally disintegrating tablet comprising (a) crystalline cellulose, (b) a calcium hydrogen phosphate compound, (c) a natural starch and (d) a lubricant, wherein the blending ratio is (a) 9 to 60 wt %, (b) 30 to 60 wt %, (c) 3 to 40 wt % and (d) 0.01 to 1.8 wt %, relative to 100 wt % of the disintegrating tablet, wherein the disintegrating tablet has an absolute hardness of not less than 1.0 N/mm$^2$ and an oral disintegration time of within 30 seconds when the disintegrating tablet is stored for 3 days at 40° C. and a relative humidity of 75%.

2. The orally disintegrating tablet according to claim 1, wherein the blending ratio of the crystalline cellulose (a) is 9 to 53 wt %, and the blending ratio of the natural starch (c) is 3 to 30 wt %.

3. The orally disintegrating tablet according to claim 1, wherein the tablet further comprises an efficacy ingredient (e) at a blending ratio of 0.01 to 60 wt %.

4. The orally disintegrating tablet according to claim 1, wherein the tablet further comprises one or more additives selected from the group consisting of fillers, binders, sweetening agents, taste correctives/odor correctives, fragrances, fluidizing agents, antistatic agents, coloring agents and coating agents.

5. The orally disintegrating tablet according to claim 3, wherein the tablet consists essentially of crystalline cellulose (a), a calcium hydrogen phosphate compound (b), a natural starch (c), a lubricant (d) and an efficacy ingredient (e).

6. The orally disintegrating tablet according to claim 3, wherein the tablet is obtained by adding a lubricant (d) to a composition obtained by blending crystalline cellulose (a), a calcium hydrogen phosphate compound (b) and a natural starch (c), each of which is in a powder or granular form, and an efficacy ingredient (e), and compression-molding the composition.

7. The orally disintegrating tablet according to claim 1, wherein the tablet is produced by compression molding by direct tableting.

8. The orally disintegrating tablet according to claim 1, wherein the blending ratio of the crystalline cellulose (a) is 20 to 53 wt %.

9. The orally disintegrating tablet according to claim 1, wherein the blending ratio of the natural starch (c) is 9 to 30 wt %.

10. The orally disintegrating tablet according to claim 1, wherein the blending ratio of the lubricant (d) is 0.01 to 1.0 wt %.

11. The orally disintegrating tablet according to claim 4, wherein the blending ratio of the additive is 0.01 to 40 wt %.

12. The orally disintegrating tablet according to claim 1, wherein the natural starch (c) is at least one kind selected from the group consisting of corn starch, wheat starch, rice starch and potato starch.

13. The orally disintegrating tablet according to claim 12, wherein the natural starch (c) is corn starch.

14. The orally disintegrating tablet according to claim 1, wherein the lubricant (d) is at least one kind selected from the group consisting of stearic acid, calcium stearate, sodium stearyl fumarate, talc, light anhydrous silicic acid and magnesium stearate.

15. The orally disintegrating tablet according to claim 14, wherein the lubricant (d) is magnesium stearate.

* * * * *